(12) United States Patent
Bush et al.

(10) Patent No.: US 11,796,530 B2
(45) Date of Patent: *Oct. 24, 2023

(54) SIMULATION AND OPTIMIZATION OF CONCRETE RECIPE

(71) Applicant: X Development LLC, Mountain View, CA (US)

(72) Inventors: Jeffrey Bush, Los Altos, CA (US); Antonio Raymond Papania-Davis, Oakland, CA (US); Weishi Yan, Seattle, WA (US); Kartikye Mittal, San Francisco, CA (US)

(73) Assignee: X Development LLC, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/934,361

(22) Filed: Sep. 22, 2022

(65) Prior Publication Data
US 2023/0100229 A1 Mar. 30, 2023

Related U.S. Application Data

(60) Provisional application No. 63/248,365, filed on Sep. 24, 2021.

(51) Int. Cl.
*G01N 33/38* (2006.01)
*G01N 11/00* (2006.01)
(Continued)

(52) U.S. Cl.
CPC .......... *G01N 33/383* (2013.01); *G01N 11/00* (2013.01); *G01N 15/14* (2013.01); *G06F 30/25* (2020.01);
(Continued)

(58) Field of Classification Search
CPC ...... G01N 33/383; G16C 60/00; G06F 30/25; G06F 2113/26; G06F 2119/02
(Continued)

(56) References Cited

U.S. PATENT DOCUMENTS 5,527,387 A    6/1996 Andersen et al.
5,943,234 A    8/1999 Martinez et al.
(Continued)

FOREIGN PATENT DOCUMENTS

CN   104926219   9/2015
CN   113392570   9/2021
(Continued)

OTHER PUBLICATIONS

Li et al. (Multi-sphere approximation of real particles for DEM simulation based on a modified greedy heuristic algorithm, Powder Technology 286 (2015) 478-487) (Year: 2015).*

(Continued)

*Primary Examiner* — Iftekhar A Khan
(74) *Attorney, Agent, or Firm* — Fish & Richardson P.C.

(57) ABSTRACT

Methods, systems, and apparatus, including computer programs encoded on computer storage media, for simulating a concrete mixture. One of the methods includes obtaining an optical characterization of physical particles, generating a multispherical approximation of the physical particles, the multispherical approximation having reduced dimensionality compared to the optical characterization, simulating an aggregate mixture by applying the multispherical approximation of the particles to a physics simulator to obtain a predicted performance of the proposed aggregate mixture, selectively altering the aggregate mixture based on a comparison with performance metrics and simulating the altered aggregate mixture until the predicted performance satisfies (Continued)

the performance metrics to obtain a final aggregate mixture, and outputting the final aggregate mixture.

20 Claims, 5 Drawing Sheets

(51) Int. Cl.
G01N 15/14 (2006.01)
G16C 60/00 (2019.01)
G06F 30/25 (2020.01)
G06F 113/26 (2020.01)
G06F 119/02 (2020.01)
G06F 113/02 (2020.01)

(52) U.S. Cl.
CPC ..... *G16C 60/00* (2019.02); *G01N 2015/1493* (2013.01); *G01N 2015/1497* (2013.01); *G06F 2113/02* (2020.01); *G06F 2119/02* (2020.01)

(58) Field of Classification Search
USPC .......................................................... 703/6
See application file for complete search history.

(56) References Cited

U.S. PATENT DOCUMENTS

| | | | |
|---|---|---|---|
| 7,104,142 B2 | 9/2006 | Martinez et al. | |
| 7,308,339 B2 | 12/2007 | Bonissone et al. | |
| 7,386,368 B2* | 6/2008 | Andersen | G06F 30/20 |
| | | | 700/265 |
| 9,533,429 B2* | 1/2017 | Phares | B28C 7/0422 |
| 9,738,562 B2 | 8/2017 | Monkman et al. | |
| 9,766,221 B2* | 9/2017 | Radjy | G01N 33/383 |
| 9,789,629 B2* | 10/2017 | Koehler | G05D 21/02 |
| 10,768,130 B2 | 9/2020 | Ghods et al. | |
| 10,865,143 B2 | 12/2020 | Ali et al. | |
| 11,332,655 B2 | 5/2022 | Morgan et al. | |
| 2008/0009976 A1* | 1/2008 | Andersen | G06F 30/13 |
| | | | 700/265 |
| 2008/0115696 A1 | 5/2008 | Compton et al. | |
| 2009/0158969 A1* | 6/2009 | Andersen | C04B 28/02 |
| | | | 106/705 |
| 2009/0239970 A1 | 9/2009 | Rodrigues et al. | |
| 2011/0004333 A1* | 1/2011 | Andersen | G05D 11/135 |
| | | | 700/265 |
| 2014/0249788 A1* | 9/2014 | Marchand | G06F 30/20 |
| | | | 703/6 |
| 2015/0142336 A1 | 5/2015 | Sant et al. | |
| 2015/0225295 A1 | 8/2015 | McCandlish et al. | |
| 2016/0223512 A1* | 8/2016 | Radjy | G01N 25/20 |
| 2018/0045621 A1* | 2/2018 | Radjy | G01N 25/00 |
| 2021/0035036 A1* | 2/2021 | Tregger | B28C 5/422 |
| 2021/0209564 A1 | 7/2021 | Di Maio et al. | |
| 2021/0253480 A1 | 8/2021 | Mahoutian | |
| 2021/0371342 A1 | 12/2021 | Salami et al. | |
| 2022/0013196 A1* | 1/2022 | Monkman | G06Q 50/08 |
| 2022/0194852 A1* | 6/2022 | Thomas | C04B 20/023 |
| 2022/0234249 A1* | 7/2022 | Papania-Davis | C04B 28/02 |
| 2022/0235258 A1 | 7/2022 | Morgan et al. | |
| 2023/0093848 A1* | 3/2023 | Nagatani | G01N 15/0205 |
| | | | 436/165 |
| 2023/0094676 A1 | 3/2023 | Papania-Davis | |
| 2023/0100229 A1* | 3/2023 | Bush | G01N 33/383 |
| | | | 703/6 |

FOREIGN PATENT DOCUMENTS

| | | |
|---|---|---|
| EP | 2026226 | 2/2009 |
| GB | 2597404 | 1/2022 |
| IN | 202241041685 | 7/2022 |
| RU | 2728755 C1 | 7/2020 |
| WO | WO 95/05350 | 2/1995 |
| WO | WO 2013/185019 | 12/2013 |
| WO | WO 2020/204954 | 10/2020 |
| WO | WO 2022/164654 | 8/2022 |

OTHER PUBLICATIONS

Amberger et al. (Approximation of Objects by Spheres for 1Viultisphere Simulations in DEM ECCOMAS 2012, pp. 1-14) (Year: 2012).*
Popescu et al. (3D reconstruction of existing concrete bridges using optical methods, Structure and Infrastructure Engineering 2019, vol. 15, No. 7, 912-924) (Year: 2019).*
Amberger et al., "Approximation of Objects by Spheres for Multisphere Simulations in DEM," European Congress on Computational Methods in Applied Sciences and Engineering (ECCOMAS 2012), Sep. 10-14, 2012, 14 pages.
Cui et al., "DEM simulation of sec flow in L-Box set-up: Influence of coarse aggregate shape on sec flowability," Cement and Concrete Composites, Feb. 11, 2020, 109:103558.
International Search Report and Written Opinion in International Appln. No. PCT/US2022/044257, dated Jan. 23, 2023, 17 pages.
Li et al., "Multi-sphere approximation of real particles for DEM simulation based on a modified greedy heuristic algorithm," Powder Technology, Dec. 1, 2015, 286:478-487.
Cheng-Qing et al., "Multi-sphere approximation of real. particl.es for DEM simulation based on a modified greedy heuristic algorithm," Powder Technology, Dec. 1, 2015, 286:478-487.
Cook et al., "Investigation of Optimize Graded Concrete for Oklahoma—Phase 1," Final Report—FHWA-OK-13-12, ODOT SP&R Item No. 2160, Oklahoma Department of Transportation, Oct. 2013, 118 pages.
Cook et al., "Investigation of Optimized Graded Concrete for Oklahoma—Phase 2," Final Report ~ FHWA-OK-15-07, ODOT SP&R Item No. 2253, Oklahoma Department of Transportation, Oct. 2015, 156 pages.
DeRousseau et al., "Computational Design Optimization of Concrete Mixtures: A Review," Cement and Concrete Research, 2018, 35 pages.
International Search Report and Written Opinion in International Appln. No. PCT/US2022/043483, dated Dec. 22, 2022, 15 pages.

* cited by examiner

SIMULATION AND OPTIMIZATION OF CONCRETE RECIPE

CROSS-REFERENCE TO RELATED APPLICATION

This application claims the benefit of the filing date of U.S. Provisional Application No. 63/248,365, filed on Sep. 24, 2021. The contents of U.S. Application No. 63/248,365 are incorporated herein by reference in their entirety.

BACKGROUND

Concrete is the second most consumed substance (by mass) on our planet and is responsible for 7-8% of global $CO_2$ emissions. Concrete's material properties are inconsistent due to the large variation in ingredient material (e.g., aggregates) and processing. This material inconsistency requires large safety margins for a given performance level and results in material overuse. Advances in concrete preparation that can optimize the use of locally available materials to maximize concrete performance while minimizing cost with both traditional and non-traditional concrete ingredients are desirable.

SUMMARY

In general, this disclosure relates to a process and system for preparing and mixing concrete to achieve target post-curing characteristics. In particular, concrete ingredients are characterized as they are measured for addition to a concrete mixture. The characterizations can be used to predict performance of a mixture formed from a combination of the ingredients. Based on the predicted performance, a recipe for the concrete mixture can be implemented.

In some examples, ingredients are characterized by a particle analyzer as they are measured and added to the concrete mixture. For example, ingredients, such as aggregates, can be monitored by a particle analyzer as they are input to a concrete mixing plant. The particle analyzer employs various sensors to detect characteristics such as particle size, particle size distribution, particle shape, and/or particle surface area. The rheometry measurements of the concrete mixture with the ingredients added can be estimated based on the measured characteristics of the ingredient.

An aggregate mix simulation system can perform extraction of lower dimensional physical characteristics of particles. The extracted lower dimensional characteristics can be used to regularize a multisphere approximation model from an auto encoder and/or to generate statistically similar models from particle databases.

A simulation system can use the approximated models to determine whether predicted performance characteristics of concrete mixtures will likely satisfy performance requirements. When the simulation system identifies a mixture that is predicted to satisfy performance requirements, the simulation system can output the identified mixture as a recommended aggregate mix recipe.

Predicting the behavior of an emulsion of particles in a fluid is challenging to do accurately. The rheological characteristics and static conditions of the fluid are especially hard to predict when the size and geometry of the particle suspended are heterogeneous. This problem is encountered in many industrial materials including concrete and asphalt where the particle size and shape distribution affect not only the liquid state but also the cured solid state. Accurately understanding fluid behavior of a using heterogeneous particle inputs is very computationally expensive without empirical experimentation.

To predictably understand and model the fluid behavior of heterogeneous particles, and the resulting cured behavior, it is tempting to characterize and attempt to accurately represent the particle inputs in simulation. While this theoretically has the best chance at an accurate result in a physics engine type simulator, the amount of characterization data and processing time to allow for thousands of unique models to be accounted for is impractical. The disclosed techniques can be used to efficiently simulate characteristics of particles in order to predict performance of a mixture of particles in both a fluid state and a cured, static state.

Particular implementations of the subject matter described in this specification can be implemented so as to realize one or more of the following advantages. Implementations may improve the operational efficiency of computers performing concrete mix simulation through the use of multisphereical approximations of particle geometry. For example, multispherical approximations of particles are a more computationally efficient way of representing the complex surfaces of aggregate particles. Multispherical approximations represent the complexities of aggregate surfaces roughness in a much less complex data set, yet can provide sufficiently accurate representations for simulation.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
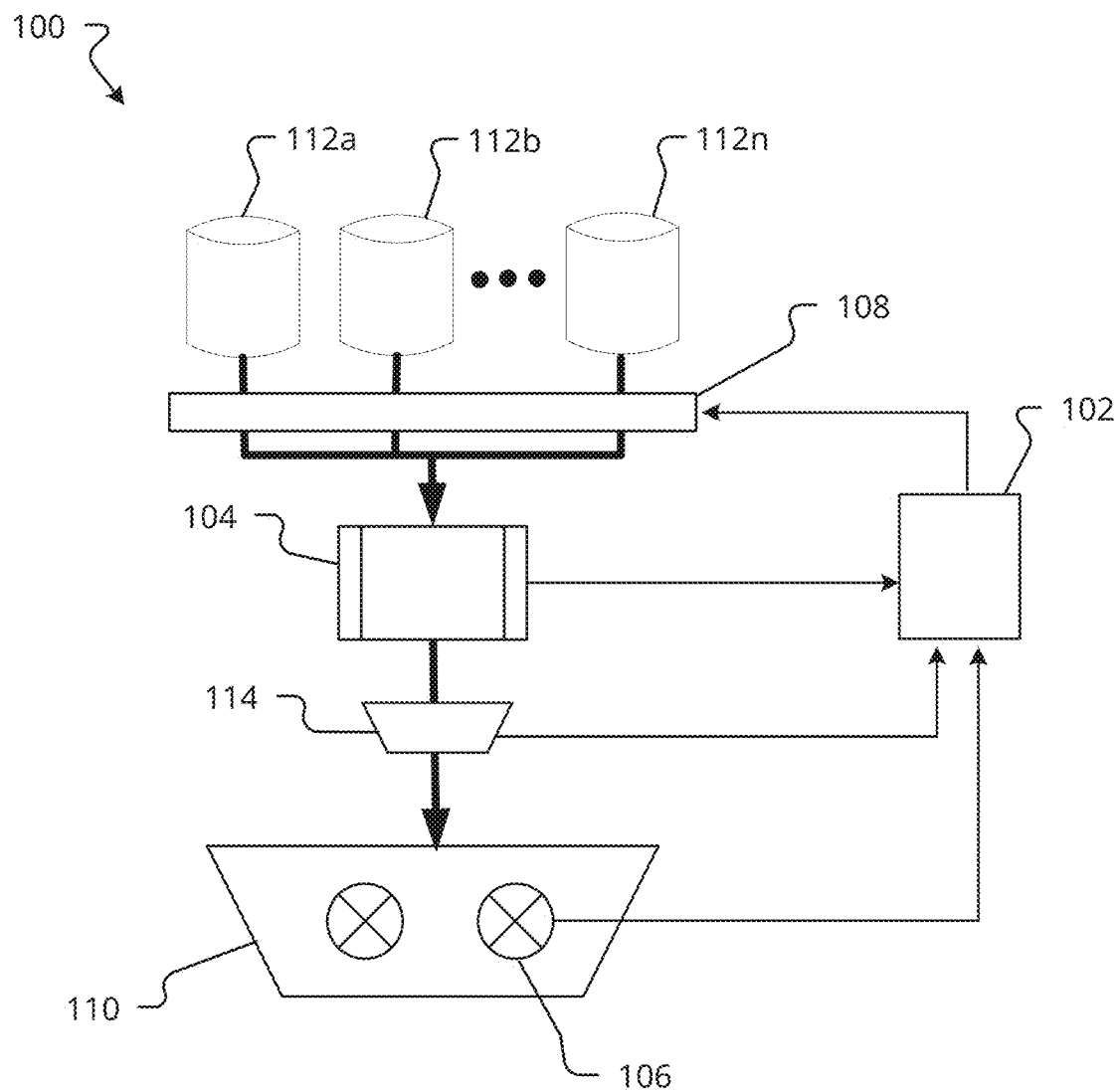
FIG. 1 depicts an exemplary concrete preparation system.

FIG. 1 depicts an exemplary concrete preparation system 100. In operation, concrete preparation system 100 measures characteristics of the raw ingredients of a concrete mixture. Concrete preparation system 100 can adaptively adjust the proportion of the raw ingredients added to the concrete mixture based on the measured characteristics to more accurately achieve desired structural properties in the final cured concrete. The operation of the system 100 is described in more detail below in reference to FIGS. 2 to 5.

Concrete preparation system 100 includes a control system 102. The control system 102 receives input from particle analyzing system 104 and concrete mix sensors 106. The control system 102 can control the operations of one or more ingredient metering systems 108 based on analyses of data obtained from one or both of the particle analyzing system 104 and concrete mix sensors 106, and based on modeling and simulation of aggregate mixes.

Concrete preparation system 100 includes raw ingredient storage bays or hoppers 112a-112n. The ingredient metering system 108 conveys the raw ingredients from the storage bays 112a-112n to a mixing vessel 110. For example, the ingredient metering system 108 can include a series of conveyors and augers to transfer raw ingredients from the storage bays 112a-112n into the mixing vessel 110. The concrete preparation system 100 differs from traditional concrete plants in that the raw ingredients are passed through the particle analyzing system 104 prior to delivery to the mixing vessel 110.

In some implementations, the ingredient metering system 108 may include a metering hopper 114 between the particle analyzing system 104 and the mixing vessel 110. The metering hopper 114 may be used to collect and measure (e.g., weigh) a raw ingredient as it passes through the particle analyzing system 104. For example, the weight of the ingredient measured by metering hopper 114 can be passed to the control system 100 permitting the control system to monitor the weight of the ingredient being measured in real-time. The control system 102 may then be able to make in-situ adjustments to how much of the ingredient to add to the concrete mixture based on real-time particle analysis of the ingredient from the particle analyzing system 104. In some implementations, concrete preparation system 100 can be retro-fit to a traditional ready-mix concrete plant. For example, adding the concrete preparation system 100 to a ready-mix plant may allow the ready-mix plant to more precisely tailor concrete mixes for specific applications and job sites.

The particle analyzing system 104 can include various different sensors configured to measure various characteristics of concrete ingredients. For example, the sensors used by the particle analyzing system 104 can include, but are not limited to, optical sensors (e.g., visible light cameras, infrared cameras, dynamic optical microscopy sensors) and mechanical sensors (e.g., sieves, sedigraphs, impact hammer, electrodynamic vibrator). The measurement data is used by the control system 102 to determine characteristics of the ingredients of the concrete mixture. For example, ingredient characteristics can include, but are not limited to, particle sizes, particle shapes, surface areas, and particle sphericity.

The sensors of the particle analyzing system 104 are arranged to obtain measurement data of concrete ingredients as the ingredients are added to a concrete mixture. For example, in some implementations optical sensors can be arranged in an array along a conveyor or a chute used to convey the raw ingredients to the mixing vessel 110. The optical sensors can transmit images of the ingredients to the control system 102, which (as explained in more detail below) can use image processing algorithms to identify particle shapes and sizes.

Some implementations may include a series of sieves to separate particles of an ingredient by size. In such implementations, the optical sensors can be positioned proximate to each sieve to capture images of the particles passing through the sieve. The images can then be used, for example, to determine an approximate count of each size range of particles exiting each sieve. In such implementations, the separated particles may be recombined before being added to the mixing vessel 110.

The concrete mix sensors 106 provide rheometry measurements of the concrete mixture to the control system 102. For example, the concrete mix sensors 106 can measure various attributes of the concrete mixture that can be used to estimate or compute rheumatic properties of the concrete mixture in real-time. The concrete mix sensors 106 can include, but are not limited to, viscosity sensors, rheometers, temperature sensors, moisture sensors, ultrasonic sensors (e.g., ultrasonic pulse velocity sensors), electrical property sensors (e.g., electrodes, electrical resistance probes), electromagnetic sensors (e.g., short-pulse radar), or other sensors (e.g., geophone, accelerometer). The concrete mix sensors 106 can include, but are not limited to, hydrophobicity, moisture content, XRD spectra, XRF spectra, static yield stress, acoustic impedance, p-wave speed, dynamic yield stress, static modulus of elasticity, Young's modulus, bulk modulus, shear modulus, dynamic modulus of elasticity (DME), Poisson's ratio, density, resonance frequency, nuclear magnetic resonance (NMR), dielectric constant, electric resistivity, polarization potential, and capacitance.

For example, viscosity, moisture, and temperature sensors can be installed in the mixing vessel 110. These sensors can be used to measure rheologic properties of the concrete mixture such as changes in the viscosity of the mixture over time and at different moisture content levels and temperatures. As described in more detail below, the control system 102 can use the rheometry measurements to determine whether and how much additional ingredients should be added to the concrete mixture to obtain desired concrete properties.

Post-curing characteristics can be determined from rheometry measurements by, e.g., using multi-dimensional lookup tables relating experimentally obtained post-curing characteristics to mixtures with known rheological properties, by applying theoretical and analytical particle packing model-based Bayesian optimization algorithms to the rheometry measurements, or a combination thereof.

In some examples, rheometry measurements can be performed on the initial concrete mixture. Rheometry measurements of the concrete mixture with the ingredients added can be estimated based on the measured characteristics of the ingredients. The rheometry measurements are used to predict characteristics of the concrete after curing.

The actual rheometry measurements of the concrete mixture can be obtained and compared with the estimated rheometry to determine whether to add additional ingredients. The system can determine, based on the rheometry measurements, whether the concrete mixture is likely to achieve a desired set of post-curing characteristics. If not, the initial mixture is adjusted through an iterative process until the rheometry measurements indicate that the concrete mixture is likely to achieve the desired post-curing characteristics.

During the iterative adjustment process, portions of concrete ingredients are incrementally added to the initial concrete mixture while changes in the rheometry measurements are monitored. Additional portions of ingredients are added until the rheometry measurements indicate that the concrete mixture is likely to achieve the desired post-curing characteristics. Such post-curing characteristics can include, but are not limited to, compressive strength, tensile/flexural strength, flowability, toughness, cure time, cure profile, finish, density (wet & dry), thermal insulation, shrinkage, and slump.

In some examples, actual performance of the concrete mixture can be compared with the predicted performance. A discrete element method (DEM) simulator can then be updated and/or trained based on the difference between the actual performance and the predicted performance.

Figure 2:
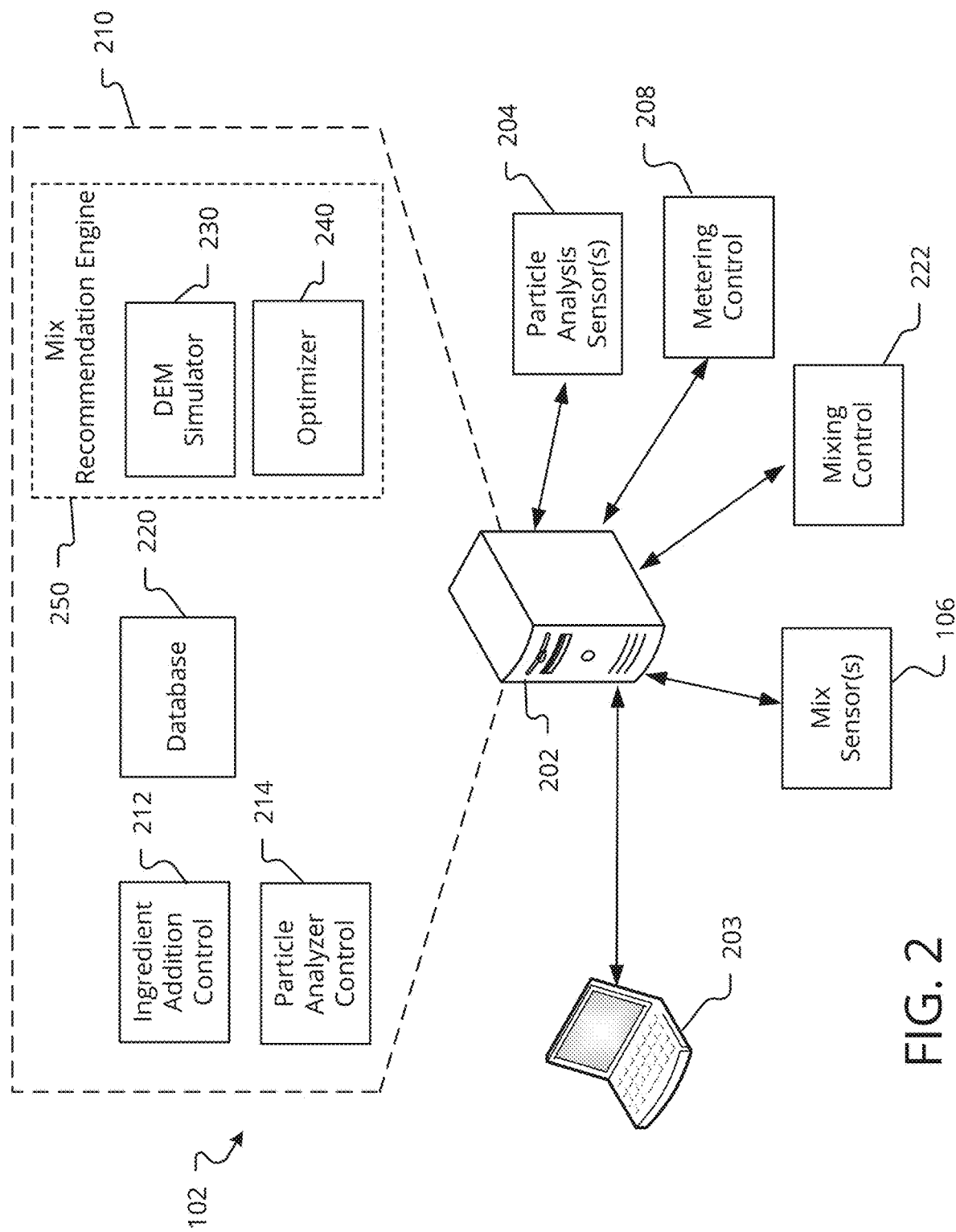
FIG. 2 depicts a block diagram of an exemplary control system for the concrete preparation system of FIG. 1.

FIG. 2 is a block diagram of an exemplary control system 102 for the concrete preparation system 100. The system 102 includes a computing system 202 in communication with the concrete mix sensors 106, particle analysis sensors 204 of the particle analyzing system 104, a metering control system 208 which can control operations of the ingredient metering system 108. Computing system 202 is configured to control various aspects of the concrete preparation process. For example, computing system 202 can store and execute one or more computer instruction sets to control the execution of aspects of the concrete preparation processes described herein. Computing system 202 can include a system of one or more computing devices. The computing devices can be, e.g., a system of one more servers. For example, a first server can be configured to receive and process data from the concrete mix sensors 106 and the particle analysis sensors 204. Another server can be configured to interface with the metering control system 208 and issue control commands based on analysis results from the first server.

In some implementations, the computing system 202 can be operated or controlled from a user computing device 203. User computing device 203 can be a computing device, e.g., desktop computer, laptop computer, tablet computer, or other portable or stationary computing device.

Briefly, computing system 202 can control the overall concrete preparation system 100 to prepare concrete mixtures. The computing system 202 can use the particle analysis sensors 204 to characterize concrete ingredients as they are added to a concrete mixture.

The computing system 202 obtains rheometry measurements from the mix sensors 106 as the concrete mixture is mixed in the mixing vessel 110. The system compares the rheometry measurements with estimated rheometry measurements to determine, e.g., whether the concrete mixture will meet desired post-curing mechanical properties or whether additional ingredients should be added.

In some implementations, computing system 202 can include a set of operations modules 210 for controlling different aspects of a concrete preparation process. The operation modules 210 can be provided as one or more computer executable software modules, hardware modules, or a combination thereof. For example, one or more of the operation modules 210 can be implemented as blocks of software code with instructions that cause one or more processors of the computing system 202 to execute operations described herein. In addition or alternatively, one or more of the operations modules can be implemented in electronic circuitry such as, e.g., programmable logic circuits, field programmable logic arrays (FPGA), or application specific integrated circuits (ASIC). The operation modules 210 can include an ingredient addition controller 212, a particle analyzer controller 214, DEM simulator 230, an optimizer 240, and one or more databases 220.

Ingredient addition controller 212 interfaces with the metering control system 208 to control the addition of ingredients to the concrete mixing vessel 110. For example, the ingredient addition controller 212 can issue commands from the computing system 202 to the metering control system 208 to control the addition of ingredients to the concrete mixture in the mixing vessel 110.

Particle analyzer control 214 interfaces with the particle analysis sensors 204 of the particle analyzing system 104. Particle analyzer controller 214 receives and buffers data from the particle analysis sensors 204. The particle analyzer controller 214 can process the sensor data to determine particle characteristics of each analyzed ingredient. For example, as discussed in more detail below, the particle analyzer controller 214 can execute data analysis algorithms to interpret the sensor data and determine particle characteristics including, but not limited to, particle size distributions, particle shape distributions, and particle surface area distributions.

The computing system 202 includes a mix recommendation engine 250. The mix recommendation engine 250 includes a DEM simulator 230 and an optimizer 240. Operations of mix recommendation engine 250 will be described in greater detail with reference to FIGS. 3 and 4.

The control system can employ DEM simulator 230 to estimate the rheometry parameters of a given concrete mixture based on the particle characteristics of the ingredients. For example, the DEM simulator 230 can employ database 220 to determine estimated rheometry measurements. The computing system can include a database 220 that correlates concrete particle characteristics to experimentally determined rheometry parameters. In some implementations, the DEM simulator 230 includes algorithms that estimate particle packing efficiencies from the particle parameters and a database 220 that correlates particle packing efficiencies with experimentally determined rheometry parameters. The computing system 202 can then compare the estimated particle packing efficiencies to the data in the database 220 to estimate the rheometry parameters of the concrete mixture.

In some implementations, DEM simulator 230 included a packing efficiency model to determine a packing efficiency of the ingredients based on the particle characteristics. The model can be a theoretical and analytical particle packing model-based Bayesian optimization algorithm—or other machine learning model—to determine a packing efficiency of the particles and estimate rheometry parameters of the mixture.

In some implementations, the DEM simulator 230 can include a machine learning model to estimate particle packing efficiency and/or rheometry parameters for a concrete mixture from measured particle characteristics. For example, the machine learning model can include a model that has been trained on experimental data to receive particle characteristics of concrete ingredients as input, and to generate a predicted output, e.g., an estimate of the particle packing efficiency, an estimate of rheometry parameters for a concrete mixture, or both. In some implementations, the machine learning model is a deep learning model that employs multiple layers of models to generate an output for a received input. A deep neural network is a deep machine learning model that includes an output layer and one or more hidden layers that each applies a non-linear transformation to a received input to generate an output. In some cases, the neural network may be a recurrent neural network. A recurrent neural network is a neural network that receives an input sequence and generates an output sequence from the input sequence. In particular, a recurrent neural network uses some or all of the internal state of the network after processing a previous input in the input sequence to generate an output from the current input in the input sequence. In some other implementations, the machine learning model is a convolutional neural network. In some implementations, the machine learning model can be a geometric inference model. In some implementations, the machine learning model is an ensemble of models that may include all or a subset of the architectures described above.

In some implementations, the machine learning model can be a feedforward autoencoder neural network. For example, the machine learning model can be a three-layer autoencoder neural network. The machine learning model may include an input layer, a hidden layer, and an output layer. In some implementations, the neural network has no recurrent connections between layers. Each layer of the neural network may be fully connected to the next, there may be no pruning between the layers. The neural network may include an ADAM optimizer, or any other multi-dimensional optimizer, for training the network and computing updated layer weights. In some implementations, the neural network may apply a mathematical transformation, such as a convolutional transformation, to input data prior to feeding the input data to the network.

In some implementations, the machine learning model can be a supervised model. For example, for each input provided to the model during training, the machine learning model can be instructed as to what the correct output should be. The machine learning model can use batch training, training on a subset of examples before each adjustment, instead of the entire available set of examples. This may improve the efficiency of training the model and may improve the generalizability of the model. The machine learning model may use folded cross-validation. For example, some fraction (the "fold") of the data available for training can be left out of training and used in a later testing phase to confirm how well the model generalizes. In some implementations, the machine learning model may be an unsupervised model. For example, the model may adjust itself based on mathematical distances between examples rather than based on feedback on its performance.

A machine learning model can be trained to estimate rheometry parameters for concrete mixtures based on measured characteristics of the ingredients to the mixture. In some examples, the machine learning model can be trained on experimentally determined data relating known characteristics of concrete ingredients to experimentally determined rheometry parameters.

The computing system 202 can store one or more databases 220 that correlate different measured parameters to experimentally determined characteristics of a concrete mixture or post-curing concrete. For example, the database 220 can include a lookup table correlating desired post-curing concrete characteristics to concrete mixture rheometry parameters, a lookup table correlating ingredient characteristics to particle packing efficiencies, and a lookup table correlating ingredient characteristics to mixture remoter parameters. Each lookup table can be a multi-dimensional data structure containing measurable concrete parameters, concrete mixture parameters, or ingredient characteristics to experimentally determined parameters.

Figure 3:
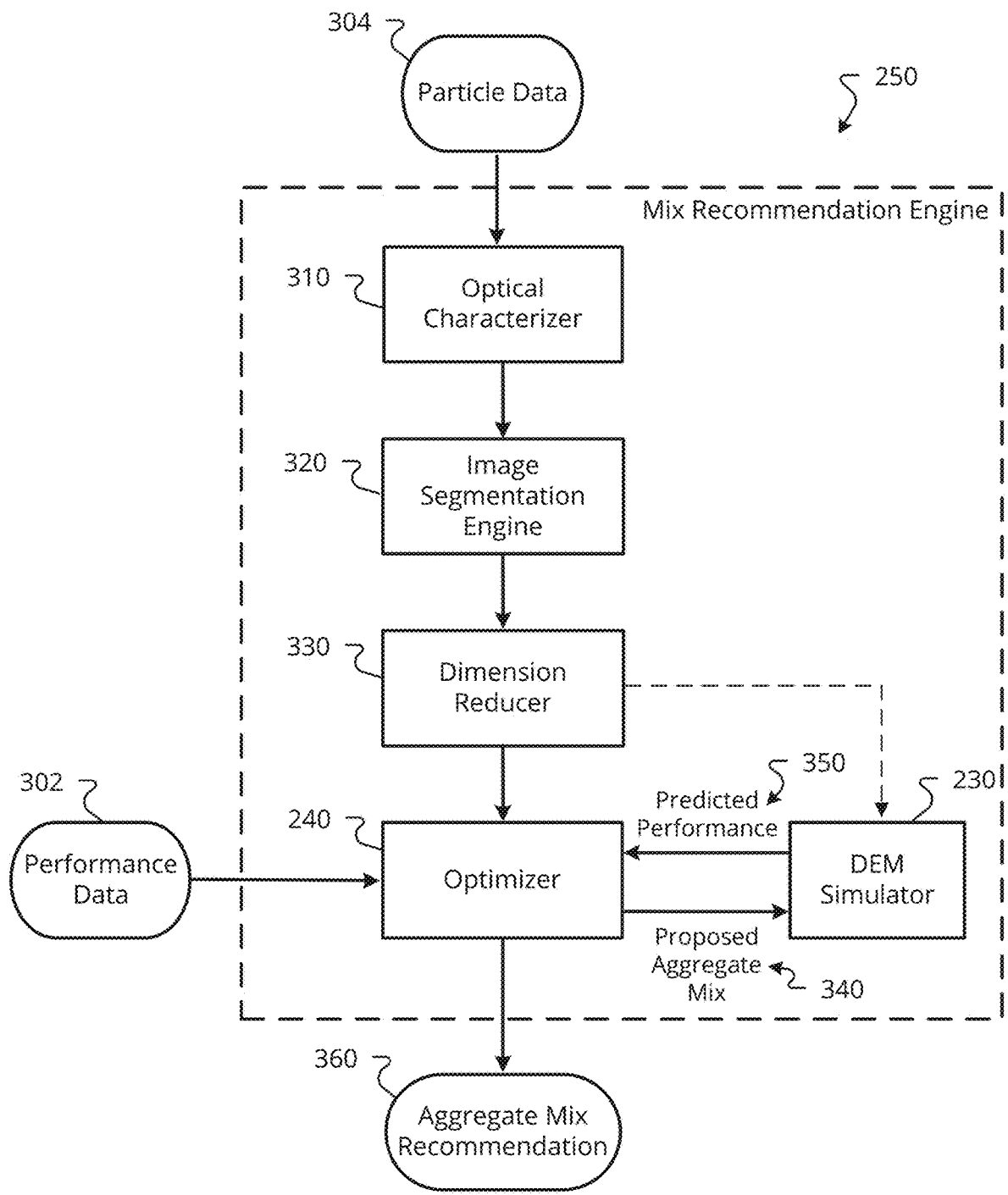
FIG. 3 depicts a block diagram of an example mix recommendation engine.

FIG. 3 illustrates a block diagram of an example mix recommendation engine 250. The mix recommendation engine 250 receives, as input, particle data 304. The particle data 304 can include sensor data from the particle analysis sensors 204. The mix recommendation engine 250 also receives, as input, performance data 302 indicating required performance characteristics of an aggregate mix.

The mix recommendation engine 250 includes an optical characterizer 310 including high precision optical characterizer hardware. The optical characterizer characterizes the particle data 304. Characteristics include but are not limited to: dimensions, elongation, flatness, angularity, and sphericity. The mix recommendation engine 250 also includes an image segmentation engine 320 for performing image segmentation and analysis on the particle data 304.

The mix recommendation engine 250 includes a dimension reducer 330. The dimension reducer 330 performs extraction of lower dimensional physical characteristics of the particle data 304. Dimension reduction is beneficial for analyzing the highly irregular geometry of aggregate due to the large number of particles in the system. In some examples, the extracted lower dimensional characteristics generated by the dimension reducer 330 can be used to regularize a multisphere approximation from an auto encoder. In some examples, the extracted lower dimensional characteristics or properties can be used to directly generate statistically similar models from databases, e.g., database 220. The lower dimensional characteristics can include, for example, elongation, flatness, angularity, sphericity, and other characteristics. Details of the multisphere approximation are discussed below in reference to FIG. 4. In some implmentations, the dimension reducer 330 includes an autoencoder such as a variational autoencoder (VAE).

The optimizer 240 receives the lower dimensional characteristics from the dimension reducer 330. The optimizer 240 generates a proposed aggregate mix 340 based on the lower dimensional characteristics and the performance data 302. The optimizer 240 provides the proposed aggregate mix 340 to the DEM simulator 230. The DEM simulator 230 determines a predicted performance 350 of the proposed aggregate mix 340.

The DEM simulator 230 outputs the predicted performance 350 to the optimizer 240. The optimizer 240 can compare the predicted performance 350 to the performance data 302. If the predicted performance 350 satisfies requirements of the performance data 302, the optimizer 240 outputs the proposed aggregate mix 340 as an aggregate mix recommendation 360. If the predicted performance 350 does not satisfy requirements of the performance data 302, the optimizer 240 can revise the recipe and provide a new proposed aggregate mix 340 to the DEM simulator 230. The optimizer 240 can continue to generate new proposed aggregate mixes 340 until the predicted performance 350 satisfies criteria specified by the performance data 302. In some implementations, the dimension reducer 330 provides the lower dimensional characteristics to the DEM simulator 230 (dashed line).

The mix recommendation engine 250 outputs the aggregate mix recommendation 360 including a recommended recipe for mixing the particles. The computing system 202 can use the aggregate mix recommendation 360 to adjust the ingredient addition controller 212. The ingredient addition controller 212 can then control addition of ingredients to the concrete mixing vessel 110 based on the aggregate mix recommendation 360.

Figure 4:
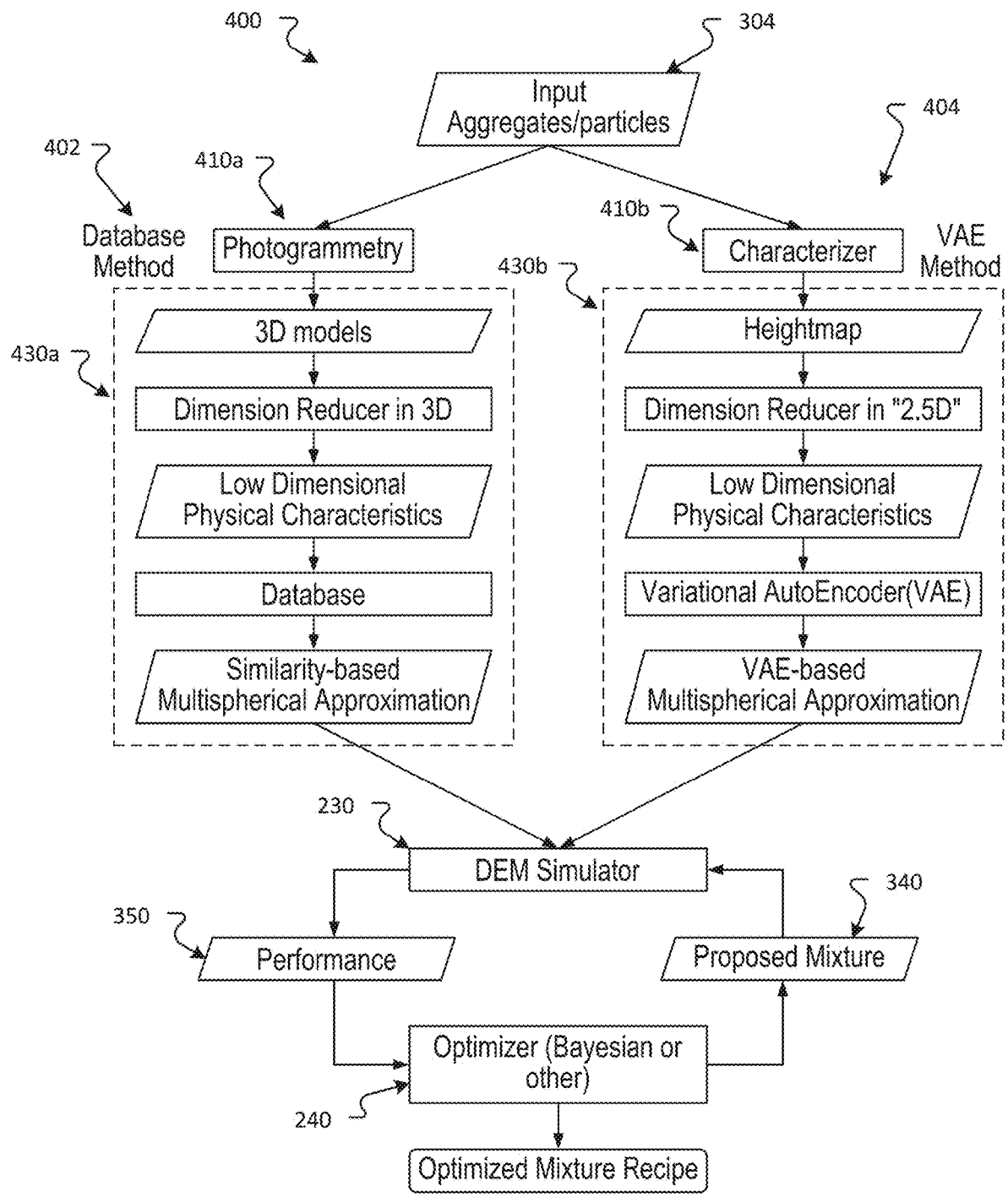
FIG. 4 illustrates example processes for generating multispherical approximations for aggregate mix modeling.

FIG. 4 illustrates an example process 400 for generating multispherical approximations for aggregate mix modeling. Simulating polyhedra with flat polygonal faces, straight edges and sharp vertices can be computationally expensive. Multi-spherical approximation of non-spherical particles can be employed to enable simplicity of contact detection while preserving meaningful physics properties.

A multispherical approximation approach is based on clumps, clusters, or clouds of overlapping or non-overlapping smaller spheres to represent a larger non-spherical irregular shape, in which internal contacts are ignored and the cluster behaves as a rigid body. Each sphere can be defined by a center coordinate location and a radius. For example, a sphere can be defined by an x-y-z coordinate of the center of the sphere, and a radius of the sphere extending from the center.

A multispherical approximation can be used to reduce resolution or fidelity of a digital representation of an object such as a particle. For example, a high fidelity digital representation of a particle can include hundreds or thousands of points and/or lines. The points and lines can approximate the surface of the particle with high accuracy. In contrast, a multispherical approximation can include tens or dozens of spheres to represent the same particle. Thus, lower fidelity digital representations, or simulations, of particles can be used, where the lower fidelity digital representations can be geometrically similar to the original characterizations.

Process 400 includes two alternative sub-processes 402 and 404 for generating low dimensional approximations of aggregates to simulate the particles. Sub-processes can be performed by the optical characterizer 310 and the dimension reducer 330. The simulated particles can be created by tuned variational auto encoding (sub-process 404) or by similarity-based recommendation from a database of characterized materials (sub-process 402), or a combination of both sub-processes. The simulated particles can capture features that, during performance simulation, produce statistically similar behaviors to higher fidelity digital representations.

Referring to sub-process 402, in some examples, photogrammetry scanning 410a is used to generate highly accurate 3D models (e.g., a surface mesh) of particles. For example, the optical characterizer 310 can employ photogrammetry to generate 3D models of particles. For example, the particle analyzer control 214 can obtain a plurality of overlapping images of the particles from a plurality of angles. The optical characterizer 310 can employ photogrammetry to generate 3D models of the particles from the sensor images. The photogrammetry 3D models are passed to the dimension reducer 330, optionally, after being processed by the image segmentation engine 320.

The dimension reducer 330 generates low dimensional physical characteristics of the particles from the photogrammetry 3D models. The dimension reducer 330 extracts lower dimensional characteristics from the 3D models 430a. For instance, the dimension reducer 330 can characterize the particles according to the elongation, flatness, angularity, and sphericity of the particles. The dimension reducer 330 can compare the extracted low dimensional physical characteristics with entries in a particle simulation database (e.g., database 220) to select a set of one or more multispherical approximations that best match the particles. The dimension reducer 330 can pass the multispherical approximations to the DEM simulator 230 or the optimizer 240 (e.g., see FIG. 3).

Referring to sub-process 404, in some examples, the optical characterizer 310 generates heightmap characterizations of aggregate particles 410b. For example, two sets of charge-coupled device (CCD) hardware and computer vision software can be used to scan aggregates quickly (e.g., particle analysis sensors 204). The optical characterizer 310 uses the scan data to generate a heightmap that contains partial information about top surface texture and geometry (e.g., a 2.5 dimensional (2.5D) representation of the particles). The height map can provide meaningful characterization about the physical properties. The heightmaps are passed to the dimension reducer 330, optionally, after being processed by the image segmentation engine 320.

The dimension reducer 330 extracts lower dimensional characteristics from the 2.5D representations of the particles 430b. The dimension reducer 330 can employ an autoencoder such as a variational autoencoder (VAE) that is trained to map a scanned particle into latent space. The VAE can decode the mapped particle to multisphere coordinates and radii. The lower dimensional physical characteristics can be used to regularize the latent space, which increases the convergence speed as well as interpretability.

In some implementations, sub-processes 402 and 404 are alternate processes. In other words, the mix control system 102 generates multispherical approximations of particles by performing either sub-process 402 or sub-process 404. In some implementations, the mix control system 102 can perform both sub-processes 402 and 404 to generate multispherical approximations of particles. In such implementations, the mix control system 102 can select to use multispherical approximations generated by either sub-process for the mix optimization and DEM simulation processes.

Using the methods described above, generation of multisphere equivalence can be generated by a physics regularized auto-encoder or by a similarity-based recommendation. The multispherical approximations can then be used to perform simulation and optimization in order to identify aggregate mixtures that satisfy performance requirements. In some examples, results of the sub-process 402 and the sub-process 404 can be used to cross-validate one another.

Mixture optimization can be performed by simulating a mixture using the lower dimensional approximation of one or more aggregates. For example, mixture optimization can be performed using a Bayesian inference network and a DEM physics simulator. The DEM simulator is a physics modeling method that can simulate static packing behavior and rheology (e.g., dynamic flow behavior). Optimization can be performed using a closed loop control system between the Bayesian inference network and the DEM simulator. The Bayesian network can predict exploration/exploitation actions as a function of uncertainty in lower feature space, while the DEM engine simulates high fidelity physical experiments and provides feedback results to a learning algorithm to iteratively improve the approximation.

Figure 5:
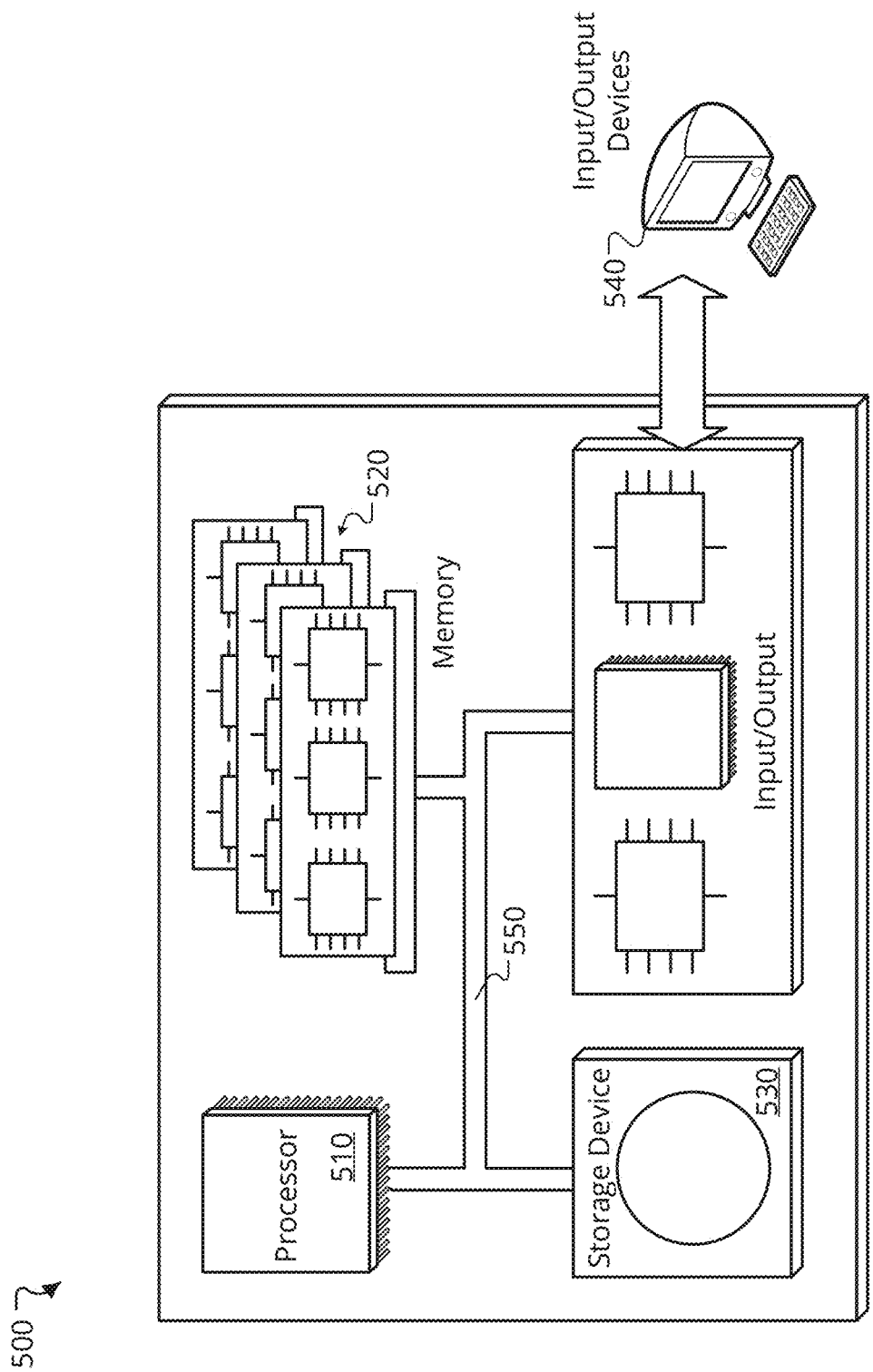
FIG. 5 depicts a schematic diagram of a computer system that may be applied to any of the computer-implemented methods and other techniques described herein.

FIG. 5 is a schematic diagram of a computer system 500. The system 500 can be used to carry out the operations described in association with any of the computer-implemented methods described previously, according to some implementations. In some implementations, computing systems and devices and the functional operations described in this specification can be implemented in digital electronic circuitry, in tangibly-embodied computer software or firmware, in computer hardware, including the structures disclosed in this specification (e.g., system 500) and their structural equivalents, or in combinations of one or more of them. The system 500 is intended to include various forms of digital computers, such as laptops, desktops, workstations, personal digital assistants, servers, blade servers, mainframes, and other appropriate computers, including vehicles installed on base units or pod units of modular vehicles. The system 500 can also include mobile devices, such as personal digital assistants, cellular telephones, smartphones, and other similar computing devices. Additionally, the system can include portable storage media, such as Universal Serial Bus (USB) flash drives. For example, the USB flash drives may store operating systems and other applications. The USB flash drives can include input/output components, such as a wireless transducer or USB connector that may be inserted into a USB port of another computing device.

The system 500 includes a processor 510, a memory 520, a storage device 530, and an input/output device 540. Each of the components 510, 520, 530, and 540 are interconnected using a system bus 550. The processor 510 is capable of processing instructions for execution within the system 500. The processor may be designed using any of a number of architectures. For example, the processor 510 may be a CISC (Complex Instruction Set Computers) processor, a RISC (Reduced Instruction Set Computer) processor, or a MISC (Minimal Instruction Set Computer) processor.

In one implementation, the processor 510 is a single-threaded processor. In another implementation, the processor 510 is a multi-threaded processor. The processor 510 is capable of processing instructions stored in the memory 520 or on the storage device 530 to display graphical information for a user interface on the input/output device 540.

The memory 520 stores information within the system 500. In one implementation, the memory 520 is a computer-readable medium. In one implementation, the memory 520 is a volatile memory unit. In another implementation, the memory 520 is a non-volatile memory unit.

The storage device 530 is capable of providing mass storage for the system 500. In one implementation, the storage device 530 is a computer-readable medium. In various different implementations, the storage device 530 may be a floppy disk device, a hard disk device, an optical disk device, or a tape device.

The input/output device 540 provides input/output operations for the system 500. In one implementation, the input/output device 540 includes a keyboard and/or pointing device. In another implementation, the input/output device 540 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Additionally, such activities can be implemented via touch-screen flat-panel displays and other appropriate mechanisms.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

As used herein, the term "ready mix" refers to concrete that is batched for delivery from a central plant instead of being mixed on a job site. Typically, a batch of ready mix is tailor-made according to the specifics of a particular construction project and delivered in a plastic condition, usually in cylindrical trucks often referred to as "concrete mixers."

As used herein, the term "real-time" refers to transmitting or processing data without intentional delay given the processing limitations of a system, the time required to accurately obtain data, and the rate of change of the data. Although there may be some actual delays, the delays are generally imperceptible to a user.

While this specification contains many specific implementation details, these should not be construed as limitations on the scope of what is being claimed, which is defined by the claims themselves, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claim may be directed to a subcombination or variation of a subcombination.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

Although the disclosed inventive concepts include those defined in the attached claims, it should be understood that the inventive concepts can also be defined in accordance with the following embodiments.

In addition to the embodiments of the attached claims and the embodiments described above, the following numbered embodiments are also innovative.

Embodiment 1 is a method of simulating a concrete mixture, the method comprising: obtaining an optical characterization of physical particles; generating a multispherical approximation of the physical particles, the multispherical approximation having reduced dimensionality compared to the optical characterization; simulating an aggregate mixture by applying the multispherical approximation of the particles to a physics simulator to obtain a predicted performance of a proposed aggregate mixture; selectively altering the aggregate mixture based on a comparison with performance metrics and simulating the altered aggregate mixture until the predicted performance satisfies the performance metrics to obtain a final aggregate mixture; and outputting the final aggregate mixture Embodiment 1 may provide one or more of technical advantages or effects. For example, the operational efficiency of computers performing concrete mix simulation through the use of multisphereical approximations of particle geometry. For example, multispherical approximations of particles are a more computationally efficient way of representing the complex surfaces of aggregate particles. Multispherical approximations represent the complexities of aggregate surfaces roughness in a much less complex data set, yet can provide sufficiently accurate representations for simulation.

Embodiment 2 is the method of embodiment 1, wherein the optical characterization comprises 3D photogrammetry models of the particles, and wherein generating the multispherical approximation comprises: applying the 3D photogrammetry models of the particles to a parcel reducer to obtain low dimensional physical characteristics of the particles; and selecting the multispherical approximation of the particles from a database by comparing the low dimensional physical characteristics to entries in the database.

Embodiment 3 is the method of any one of embodiments 1 through 2, wherein the optical characterization comprises heightmap representations of the particles, and wherein generating the multispherical approximation comprises: applying the heightmap representations of the particles to a parcel reducer to obtain low dimensional physical characteristics of the particles; and determining the multispherical approximation of the particles by applying the low dimensional physical characteristics of the particles to an autoencoder.

Embodiment 4 is the method of any one of embodiments 1 through 3, wherein the physics simulator comprises a Bayesian inference network and a discrete element method (DEM) simulator.

Embodiment 5 is the method of any one of embodiments 1 through 4, further comprising: controlling an ingredient metering system to measure and add a plurality of ingredients to a concrete mixture based on the final aggregate mixture; measuring, using a particle analyzer, characteristics of at least one ingredient of the ingredients; determining, based on the measured characteristics, an estimated rheometry measurement of for the concrete mixture by: generating multispherical approximations of the ingredients based on the measured characteristics, and simulating the concrete mixture containing the plurality of ingredients by applying the multispherical approximations of the ingredients to the physics simulator to obtain the estimated rheometry measurement; obtaining an actual rheometry measurement of the concrete mixture; and selectively controlling the ingredient metering system to add one or more additional ingredients to the concrete mixture based on a comparison of the estimated rheometry measurement with the actual rheometry measurement.

Embodiment 6 is the method of embodiment 5, wherein the characteristics of the at least one ingredient comprises one or more of a particle size distribution, a particle shape distribution, or particle sphericity.

Embodiment 7 is the method of embodiment 6, wherein determining an estimated rheometry measurement of the concrete mixture comprises determining, based on the characteristics, a particle packing efficiency for the at least one ingredient, and determining the estimated rheometry measurement based at least in part on the particle packing efficiency.

Embodiment 8 is the method of embodiment 7, wherein determining the estimated rheometry measurement based at least in part on the particle packing efficiency comprises comparing the particle packing efficiency to a multi-dimensional lookup table that associates particle packing efficiencies to experimentally determined expected rheometry measurements.

Embodiment 9 is the method of embodiment 7, wherein determining the particle packing efficiency comprises applying characteristics as input to a Bayesian optimization algorithm.

Embodiment 10 is the method of any one of embodiments 5 through 7, further comprising: iteratively adjusting the concrete mixture until a stop condition is achieved, wherein each iteration comprises: obtaining rheometry measurements of the concrete mixture; determining, based on the rheometry measurements, whether the concrete mixture satisfies the stop condition; in response to the rheometry measurements not satisfying the stop condition: determining additional portions for one or more of the ingredients to be added to the concrete mixture in order to meet a set of target concrete characteristics, and controlling the ingredient metering system to measure and add the additional portions to the concrete mixture; and in response to determining that the concrete mixture satisfies the stop condition, ceasing the iteratively adjusting the concrete mixture.

Embodiment 11 is the method of embodiment 10, wherein the stop condition is the set of target concrete characteristics.

Embodiment 12 is the method of any one of embodiments 10 through 11, wherein determining whether the concrete mixture satisfies the stop condition comprises determining whether the rheometry measurements indicate that the concrete mixture is likely to achieve at least one of the set of target concrete characteristics within a threshold value.

Embodiment 13 is the method of embodiment 12, wherein determining whether the rheometry measurements indicate that the concrete mixture is likely to achieve at least one of the set of target concrete characteristics comprises: determining target rheometry parameters based on a multi-dimensional lookup table associating experimentally obtained post-curing characteristics to concrete mixtures with known rheological properties; and comparing the rheometry measurements to the target rheometry parameters.

Embodiment 14 is a system comprising: one or more computers and one or more storage devices storing instructions that are operable, when executed by the one or more computers, to cause the one or more computers to perform the method of any one of claims 1 to 13.

Embodiment 15 is a computer storage medium encoded with a computer program, the program comprising instructions that are operable, when executed by data processing apparatus, to cause the data processing apparatus to perform the method of any one of claims 1 to 13.

The invention claimed is:

1. A method of simulating a concrete mixture, the method comprising:
obtaining an optical characterization of physical particles;
generating a multispherical approximation of the physical particles, the multispherical approximation having reduced dimensionality compared to the optical characterization;
simulating an aggregate mixture by applying the multispherical approximation of the particles to a physics simulator to obtain a predicted performance of a proposed aggregate mixture;
selectively altering the aggregate mixture based on a comparison with performance metrics and simulating the altered aggregate mixture until the predicted performance satisfies the performance metrics to obtain a final aggregate mixture, wherein the performance metrics comprise concrete post-curing characteristics; and
outputting the final aggregate mixture.

2. The method of claim 1, wherein the optical characterization comprises 3D photogrammetry models of the particles, and wherein generating the multispherical approximation comprises:
applying the 3D photogrammetry models of the particles to a parcel dimension reducer to obtain low dimensional physical characteristics of the particles; and
selecting the multispherical approximation of the particles from a database by comparing the low dimensional physical characteristics to entries in the database.

3. The method of claim 1, wherein the optical characterization comprises heightmap representations of the particles, and wherein generating the multispherical approximation comprises:
applying the heightmap representations of the particles to a parcel dimension reducer to obtain low dimensional physical characteristics of the particles; and
determining the multispherical approximation of the particles by applying the low dimensional physical characteristics of the particles to an autoencoder.

4. The method of claim 1, wherein the physics simulator comprises a Bayesian inference network and a discrete element method (DEM) simulator.

5. The method of claim 1 further comprising:
controlling an ingredient metering system to measure and add a plurality of ingredients to a concrete mixture based on the final aggregate mixture;
measuring, using a particle analyzer, characteristics of at least one ingredient of the ingredients;
determining, based on the measured characteristics, an estimated rheometry measurement of for the concrete mixture by:
generating multispherical approximations of the ingredients based on the measured characteristics, and
simulating the concrete mixture containing the plurality of ingredients by applying the multispherical approximations of the ingredients to the physics simulator to obtain the estimated rheometry measurement;
obtaining an actual rheometry measurement of the concrete mixture; and
selectively controlling the ingredient metering system to add one or more additional ingredients to the concrete mixture based on a comparison of the estimated rheometry measurement with the actual rheometry measurement.

6. The method of claim 5, wherein the characteristics of the at least one ingredient comprises one or more of a particle size distribution, a particle shape distribution, or particle sphericity.

7. The method of claim 6, wherein determining an estimated rheometry measurement of the concrete mixture comprises determining, based on the characteristics, a particle packing efficiency for the at least one ingredient, and determining the estimated rheometry measurement based at least in part on the particle packing efficiency.

8. The method of claim 7, wherein determining the estimated rheometry measurement based at least in part on the particle packing efficiency comprises comparing the particle packing efficiency to a multi-dimensional lookup table that associates particle packing efficiencies to experimentally determined expected rheometry measurements.

9. The method of claim 7, wherein determining the particle packing efficiency comprises applying characteristics as input to a Bayesian optimization algorithm.

10. The method of claim 5, further comprising:
iteratively adjusting the concrete mixture until a stop condition is achieved, wherein each iteration comprises:
  obtaining rheometry measurements of the concrete mixture;
  determining, based on the rheometry measurements, whether the concrete mixture satisfies the stop condition;
  in response to the rheometry measurements not satisfying the stop condition:
    determining additional portions for one or more of the ingredients to be added to the concrete mixture in order to meet a set of target concrete characteristics, and
    controlling the ingredient metering system to measure and add the additional portions to the concrete mixture; and
  in response to determining that the concrete mixture satisfies the stop condition, ceasing the iteratively adjusting the concrete mixture.

11. The method of claim 10, wherein the stop condition is the set of target concrete characteristics.

12. The method of claim 10, wherein determining whether the concrete mixture satisfies the stop condition comprises determining whether the rheometry measurements indicate that the concrete mixture is likely to achieve at least one of the set of target concrete characteristics within a threshold value.

13. The method of claim 12, wherein determining whether the rheometry measurements indicate that the concrete mixture is likely to achieve at least one of the set of target concrete characteristics comprises:
  determining target rheometry parameters based on a multi-dimensional lookup table associating experimentally obtained post-curing characteristics to concrete mixtures with known rheological properties; and
  comparing the rheometry measurements to the target rheometry parameters.

14. A system comprising:
at least one processor; and a data store coupled to the at least one processor having instructions stored thereon which, when executed by the at least one processor, causes the at least one processor to perform operations comprising:
obtaining an optical characterization of physical particles;
generating a multispherical approximation of the physical particles, the multispherical approximation having reduced dimensionality compared to the optical characterization;
simulating an aggregate mixture by applying the multispherical approximation of the particles to a physics simulator to obtain a predicted performance of a proposed aggregate mixture;
selectively altering the aggregate mixture based on a comparison with performance metrics and simulating the altered aggregate mixture until the predicted performance satisfies the performance metrics to obtain a final aggregate mixture, wherein the performance metrics comprise concrete post-curing characteristics; and
outputting the final aggregate mixture.

15. The system of claim 14, wherein the optical characterization comprises 3D photogrammetry models of the particles, and wherein generating the multispherical approximation comprises:
  applying the 3D photogrammetry models of the particles to a parcel dimension reducer to obtain low dimensional physical characteristics of the particles; and
  selecting the multispherical approximation of the particles from a database by comparing the low dimensional physical characteristics to entries in the database.

16. The system of claim 14, wherein the optical characterization comprises heightmap representations of the particles, and wherein generating the multispherical approximation comprises:
  applying the heightmap representations of the particles to a parcel dimension reducer to obtain low dimensional physical characteristics of the particles; and
  determining the multispherical approximation of the particles by applying the low dimensional physical characteristics of the particles to anautoencoder.

17. The system of claim 14, wherein the physics simulator comprises a Bayesian inference network and a discrete element method (DEM) simulator.

18. The system of claim 14 the operations further comprising:
  controlling an ingredient metering system to measure and add a plurality of ingredients to a concrete mixture based on the final aggregate mixture;
  measuring, using a particle analyzer, characteristics of at least one ingredient of the ingredients;
  determining, based on the measured characteristics, an estimated rheometry measurement of for the concrete mixture by:
    generating multispherical approximations of the ingredients based on the measured characteristics, and
    simulating the concrete mixture containing the plurality of ingredients by applying the multispherical approximations of the ingredients to the physics simulator to obtain the estimated rheometry measurement;
  obtaining an actual rheometry measurement of the concrete mixture; and
  selectively controlling the ingredient metering system to add one or more additional ingredients to the concrete mixture based on a comparison of the estimated rheometry measurement with the actual rheometry measurement.

19. The system of claim 18, wherein the characteristics of the at least one ingredient comprises one or more of a particle size distribution, a particle shape distribution, or particle sphericity,
  wherein determining an estimated rheometry measurement of the concrete mixture comprises determining, based on the characteristics, a particle packing efficiency for the at least one ingredient, and determining the estimated rheometry measurement based at least in part on the particle packing efficiency, and
  wherein determining the estimated rheometry measurement based at least in part on the particle packing efficiency comprises comparing the particle packing efficiency to a multi-dimensional lookup table that associates particle packing efficiencies to experimentally determined expected rheometry measurements.

20. A non-transitory computer readable storage medium storing instructions that, when executed by at least one processor, cause the at least one processor to perform operations comprising:
- obtaining an optical characterization of physical particles;
- generating a multispherical approximation of the physical particles, the multispherical approximation having reduced dimensionality compared to the optical characterization;
- simulating an aggregate mixture by applying the multispherical approximation of the particles to a physics simulator to obtain a predicted performance of a proposed aggregate mixture;
- selectively altering the aggregate mixture based on a comparison with performance metrics and simulating the altered aggregate mixture until the predicted performance satisfies the performance metrics to obtain a final aggregate mixture, wherein the performance metrics comprise concrete post-curing characteristics; and
- outputting the final aggregate mixture.

* * * * *